United States Patent
Campbell et al.

(10) Patent No.: US 9,772,279 B2
(45) Date of Patent: Sep. 26, 2017

(54) SENSOR FOR CONTINUOUS, REAL-TIME MONITORING OF CARBON DIOXIDE FOR CHEMICAL CONTAMINANTS

(71) Applicant: The Coca-Cola Company, Atlanta, GA (US)

(72) Inventors: Daniel P. Campbell, Atlanta, GA (US); Jayme Caspall, Decatur, GA (US); Janet Cobb-Sullivan, Marietta, GA (US); Kenneth E. Johnson, Kennesaw, GA (US); Robert E. Jones, Atlanta, GA (US); Larry Starr, Colorado Springs, GA (US); Michael Slawson, Atlanta, GA (US); Ruoya Wang, Marietta, GA (US)

(73) Assignee: The Coca-Cola Company, Atlanta, GA (US)

(*) Notice: Subject to any disclaimer, the term of this patent is extended or adjusted under 35 U.S.C. 154(b) by 0 days.

(21) Appl. No.: 14/622,886

(22) Filed: Feb. 15, 2015

(65) Prior Publication Data

US 2015/0300952 A1    Oct. 22, 2015

Related U.S. Application Data

(60) Provisional application No. 61/940,250, filed on Feb. 14, 2014.

(51) Int. Cl.
*G01N 21/45* (2006.01)
*G05D 7/00* (2006.01)
*G01N 21/41* (2006.01)
*G01N 21/77* (2006.01)
*G01N 21/94* (2006.01)
*G01N 21/17* (2006.01)
*G01N 33/00* (2006.01)

(52) U.S. Cl.
CPC ............ *G01N 21/41* (2013.01); *G01N 21/45* (2013.01); *G01N 21/7703* (2013.01); *G01N 21/94* (2013.01); *G05D 7/00* (2013.01); *G01N 33/004* (2013.01); *G01N 33/0044* (2013.01); *G01N 33/0047* (2013.01); *G01N 2021/1765* (2013.01); *G01N 2021/773* (2013.01); *G01N 2021/7716* (2013.01); *G01N 2021/7776* (2013.01); *G01N 2021/7779* (2013.01); *G01N 2201/06113* (2013.01); *G01N 2201/08* (2013.01)

(58) Field of Classification Search
CPC .... G01N 21/41; G01N 21/45; G01N 21/7703; G01N 21/94; G01N 2021/7779; G05D 7/00

See application file for complete search history.

(56) References Cited

U.S. PATENT DOCUMENTS 7,064,834 B2   6/2006   Johnson et al.
7,631,568 B2   12/2009  Kilps et al.
(Continued)

*Primary Examiner* — Michael A Lyons
*Assistant Examiner* — Violeta A Prieto
(74) *Attorney, Agent, or Firm* — Eversheds Sutherland (US) LLP

(57) ABSTRACT

A system and method for the monitoring of carbon dioxide (CO2) for chemical contaminants. The carbon dioxide monitoring system includes a contaminant sensor that is configured to detect trace amounts of contaminants in CO2 that is pumped through it in real time. The contaminant sensor includes an interferometer configured to track the amount of contaminants.

19 Claims, 13 Drawing Sheets

(56) References Cited

U.S. PATENT DOCUMENTS

| | | | |
|---|---|---|---|
| 7,820,108 B2 | 10/2010 | Lampotang et al. | |
| 2003/0197852 A1* | 10/2003 | Johnson | C01B 31/20 356/37 |
| 2007/0147732 A1* | 6/2007 | Sanders | B82Y 20/00 385/32 |
| 2008/0049231 A1* | 2/2008 | Bachalo | G01N 15/1459 356/484 |
| 2008/0231857 A1 | 9/2008 | Depeursing et al. | |
| 2011/0149294 A1* | 6/2011 | Song | G01N 21/45 356/477 |
| 2011/0305599 A1* | 12/2011 | Tan | G01N 21/45 422/69 |
| 2012/0214707 A1 | 8/2012 | Ymeti et al. | |
| 2014/0311350 A1* | 10/2014 | Campbell | G01N 21/7703 96/417 |
| 2015/0077756 A1* | 3/2015 | Campbell | G01N 33/1826 356/450 |

\* cited by examiner

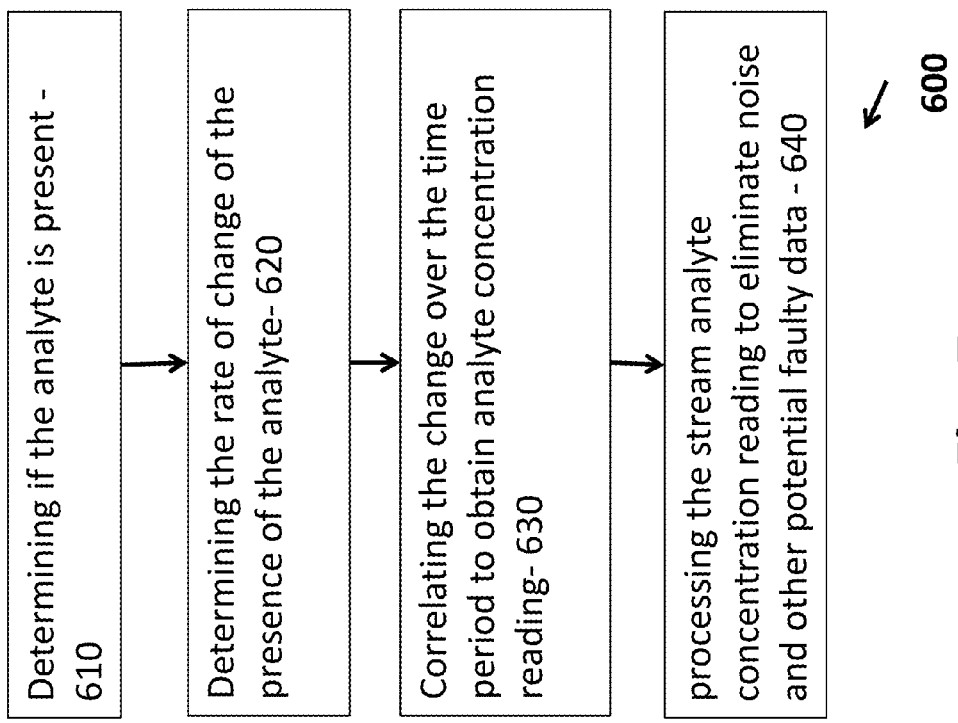

SENSOR FOR CONTINUOUS, REAL-TIME MONITORING OF CARBON DIOXIDE FOR CHEMICAL CONTAMINANTS

CROSS-REFERENCE TO RELATED APPLICATIONS

This application claims priority to U.S. Provisional Patent Application No. 61/940,250, filed Feb. 14, 2014, which is relied upon and is hereby incorporated by reference in its entirety by reference.

BACKGROUND OF THE INVENTION

Carbon dioxide gas, used in carbonated beverages, in food packaging, and in disinfection, is occasionally found, at the point of use, to be contaminated with compounds that can affect the taste, smell, and even the safety of the food or beverage product with which it is being used. The numerous, often localized, processes of manufacturing or acquiring carbon dioxide gas are often imperfect in their ability to generate fully pure carbon dioxide, and methods of cleaning or "scrubbing" the gas occasionally fail. Pure carbon dioxide can then become contaminated upon storage or transport, particularly if it is placed in previously contaminated containers.

Contaminated carbon dioxide can contain a wide range of contaminants, including acetaldehyde, sulfur compounds, aromatic hydrocarbons like benzene, and other volatile hydrocarbons like methane. Most contaminants, in moderate levels, only result in negative taste and smell impacts to the products using the carbon dioxide. In high levels some contaminants are toxic and can cause illness and even death. Benzene and a few others are, in moderate levels, believed to be carcinogenic.

The International Society of Beverage Technologists (ISBT), a beverage industry organization with over 1,000 corporate members, has developed guidelines for acceptable contamination levels in nonalcoholic beverages and soft drinks. These guidelines recommend maximum concentration levels for thirteen compounds or compound families including, for example, that acetaldehyde concentrations never exceed 200 parts-per-billion and that aromatic hydrocarbon concentrations never exceed 20 parts-per-billion.

However, the continuous or near-continuous monitoring of carbon dioxide in a production environment is currently very costly. Carbon dioxide analyzers on the market are built around chemical analysis equipment employing gas chromotography (GC) and mass spectroscopy (MS), more commonly found in laboratories. Carbon dioxide analyzer companies ruggedize these GC/MS units and augment them with peripheral electronic equipment to regulate sample flow and automate their measurement functions. These systems can easily cost $200,000 or more. They comprise one or more racks of equipment in an enclosure that can be five or six feet tall and weigh hundreds of pounds.

In addition to their high cost, current carbon dioxide analyzers are often touchy and expensive to maintain. Some require the use of "carrier" gases, including hydrogen, which is highly explosive. Carrier and "span" gases used in calibration can routinely cost $6,000 per year. The units typically sample the carbon dioxide flow at a rate of once every ten to twenty minutes, which may not be fast enough to catch fast contaminant transients, or eliminate all chance of product contamination.

Therefore, there is a need for a compact, robust, and inexpensive monitor that can make accurate and near-real-time measurements, thus dramatically reducing cost while enabling carbon dioxide producers and users to better assess and reduce contamination risk.

SUMMARY OF THE INVENTION

The present invention provides a carbon dioxide monitoring system. The carbon dioxide monitoring system includes a sensor that is configured to detect the presence of contaminants, which can include, but are not limited to, acetaldehyde, aromatic hydrocarbons (benzene, toluene, ethylbenzene, and xylene), sulfur compounds, and volatile hydrocarbons (like methane), in a flow of carbon dioxide gas. In an aspect, the sensor is configured to detect and report the particular level of a contaminant whose concentration exceeds ISBT standards. In another aspect, the sensor is configured to raise an alarm if the concentration of any contaminant exceeds an ISBT standard.

In an aspect, the carbon dioxide monitoring system is configured to be fully automated. In an aspect, the carbon dioxide monitoring system is configured to continually monitor the carbon dioxide line, or to evaluate samples of the carbon dioxide at a period sufficiently faster than the rate at which the contaminant level in the carbon dioxide can materially change. In another aspect, the carbon dioxide monitoring system is ruggedly configured to work reliably and robustly in industrial applications, to include beverage bottling facilities and carbon dioxide generation plants.

These and other objects and advantages of the invention will become apparent from the following detailed description of the preferred embodiment of the invention.

Both the foregoing general description and the following detailed description are exemplary and explanatory only and are intended to provide further explanation of the invention as claimed. The accompanying drawings are included to provide a further understanding of the invention and are incorporated in and constitute part of this specification, illustrate several embodiments of the invention, and together with the description serve to explain the principles of the invention.

BRIEF DESCRIPTION OF THE DRAWINGS

FIG. 7 is a flow diagram of a method performed by a carbon dioxide monitoring system according to an aspect of the present invention.

DETAILED DESCRIPTION OF THE PREFERRED EMBODIMENTS

Figure 1:
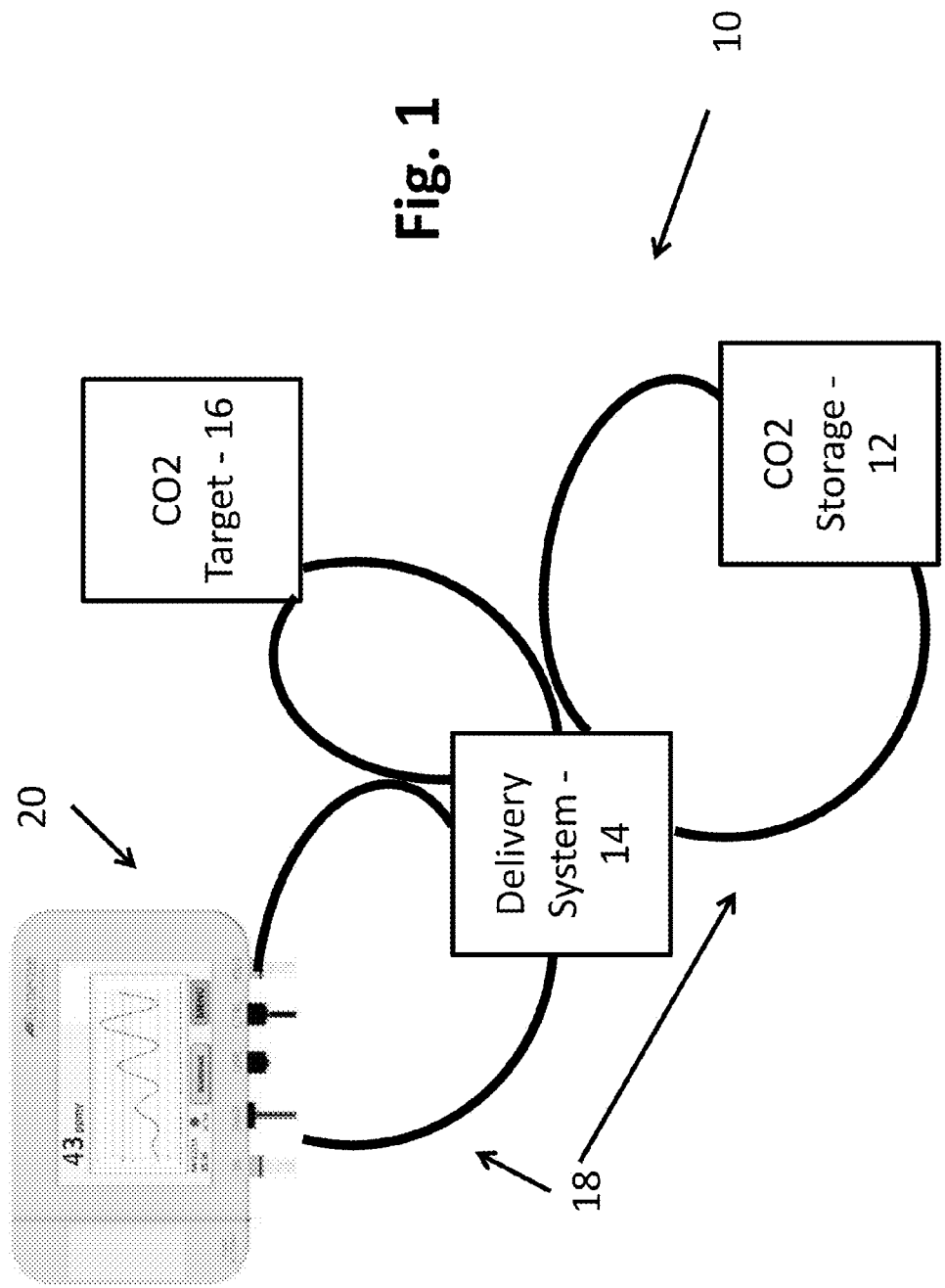
FIG. 1 is a schematic view of a carbon dioxide monitoring system utilizing a real-time sensor according to an aspect.

Before the present methods and systems are disclosed and described, it is to be understood that the methods and systems are not limited to specific synthetic methods, specific components, or to particular compositions. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other additives, components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer readable memory that can direct a computer or other programmable data processing apparatus to function in a particular manner, such that the instructions stored in the computer-readable memory produce an article of manufacture including computer readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions, and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Figure 2:
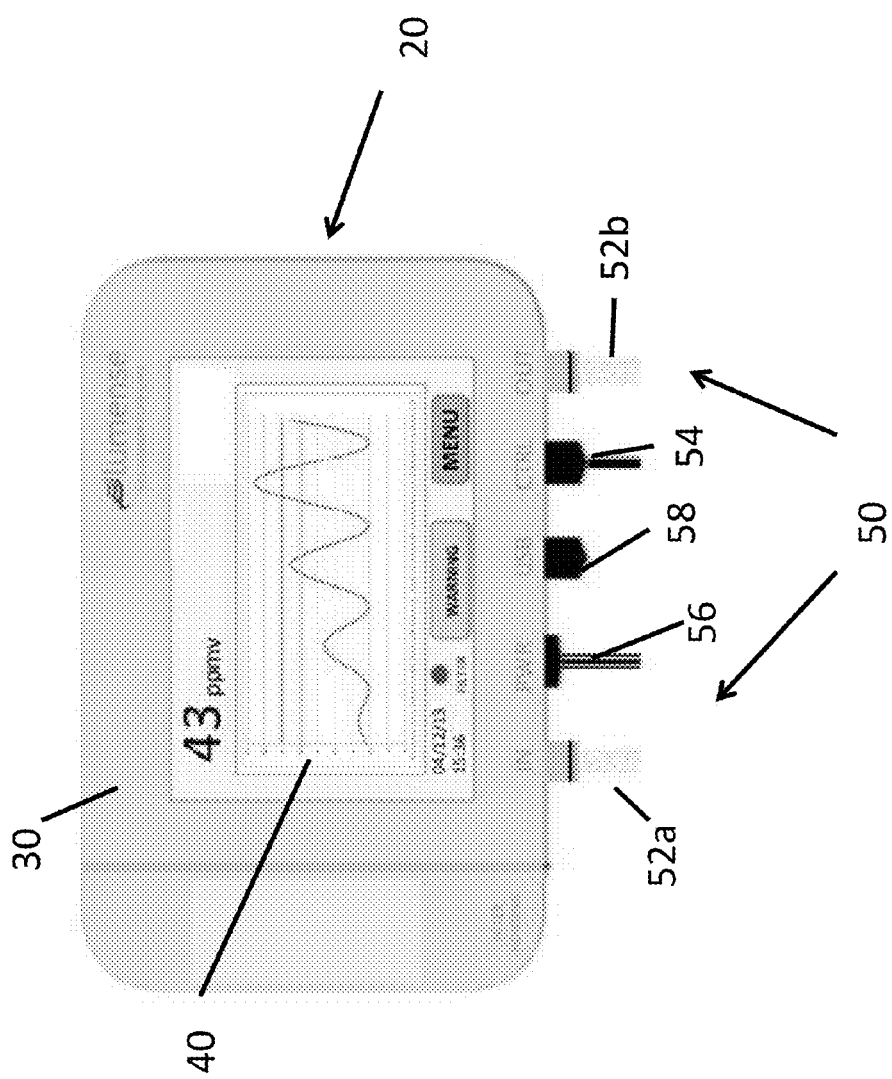
FIG. 2 is a front plan view of the real-time sensor of FIG. 1.

Referring to FIGS. 1 and 2, the present invention is directed to a carbon dioxide monitoring system 10 configured to monitor carbon dioxide for contaminants in real time. In an exemplary aspect, the carbon dioxide monitoring system 10 is configured for monitoring carbon dioxide in a beverage plant. In other aspects, the carbon dioxide monitoring system 10 can be used in a variety of settings in which the continuous monitoring for contaminants in a fluid (i.e., gas or liquid) is needed. For example, the carbon dioxide monitoring system 10 can be configured for use in food packaging facilities, or carbon dioxide generation or extraction plants or distilleries.

In an aspect, the carbon dioxide monitoring system 10 is configured to be capable of being located near a carbon dioxide storage or transport tank 12, and of receiving a continuous flow of carbon dioxide from that tank 12. In an aspect, the carbon dioxide monitoring system 10 includes a delivery system 14 to deliver the monitored carbon dioxide to a carbon dioxide target 16 and the real-time contaminant sensor 20. In an aspect, the delivery system 14 can be any type of system utilized in delivering/transporting carbon dioxide from storage to the location of the carbon dioxide's application.

In an aspect, the carbon dioxide monitoring system 10 is further configured to be employed at industrial locations. In such aspects, the carbon dioxide monitoring system 10 can be configured for wired or wireless communications using a wireless radio. For example, the wired communications can include, but are not limited to, LANs, T1 lines, intranets, and Ethernet, while the wireless communications can include, but are not limited to, cellular communication means (CDMA, GPRS, LTE, etc.), Bluetooth, Wi-Fi, satellite, and other types of wireless connectivity.

In an aspect, the delivery system 14 of the carbon dioxide monitoring system 10 is configured to deliver the monitored carbon dioxide to the contaminant sensor 20. The delivery system 14 can include tubing/piping 18 that tap into the carbon dioxide storage 12 and/or delivery system 14, and may be selected and altered (e.g. passivated) depending on the types of contamination believed to be present. Such tubing 18 can include, but is not limited to, stainless steel, aluminum, PVC, Tygon, PTFE, polyethylene, and the like. In an aspect, the tubing 16 can be of a flexible nature in order to avoid any potential obstructions between the contaminant sensor 20 and the carbon dioxide line 12. Various fastening means, including, but not limited to, mounting brackets, may be used to secure the components of the delivery system 14, including the tubing 16, in place at the monitoring site. While the contaminant sensor 20 can be mounted at various locations near the carbon dioxide storage 12 and target 14, it is preferable that it is placed at a position of easy access for routine maintenance, if needed. The setup of the carbon dioxide monitoring system 10 is not limited to the just described configurations, and can be oriented in various positions based upon the needs of the location of monitoring.

In an aspect, as shown in FIG. 2, the contaminant sensor 20 includes a housing 30, a user interface 40, and external connections 50. The housing 30 of the contaminant sensor 20 is configured to contain various hardware and software components discussed in further detail below. In an aspect, the carbon dioxide monitoring system 10 is configured for use of the monitoring of carbon dioxide delivery systems 14 used in factory environments, with the housing 30 can be made of a rugged and rigid material. The sturdy material can include, but is not limited to, sheet metal, aluminum, molded plastic, and other similar materials that are sufficient to protect the inner components of the contaminant sensor 20 and meet safety and regulatory requirements. The material of the housing 30 of the contaminant sensor 20 can include any material that will safely protect the internal components of the contaminant sensor 20 as discussed in detail below. In an aspect, the housing 30 can include a removable cover, giving access to certain components of the contaminant sensor 20, including filters used to filter targeted contaminants and waveguides, discussed in detail below. In an exemplary aspect of the present invention, the housing 30 is configured to notify (e.g., via a switch) the various hardware and software components of the contaminant sensor 20 when the cover is removed or reinstalled.

As discussed above, in an aspect, the contaminant sensor 20 can include a user interface 40. In such an aspect, the user interface 40 comprises a single, large, backlit color touchscreen on which all user controls and displays reside. While the preferred embodiment of the present invention uses an interactive touchscreen 40, the contaminant sensor 20 can include other types of user interfaces 40, including, but not limited to, a combination keypad and display screen, and the like. In some embodiments of the present invention, it may be desirable for the contaminant sensor 20 not to have any direct human-accessible interface, limiting the control of the contaminant sensor 20 to authorized individuals remotely through a wireless or wired connection, discussed in more detail below. Specific controls and displays, and their functions, are discussed in more detail below. While the dimensions of the user interface 40 and the overall housing 30 can be of various combinations, in one embodiment the touchscreen 40 is approximately 6"×4.5" and the housing 30 is 7"×9" in area, and 3" deep.

As shown in FIG. 2, the contaminant sensor 20 provides external connections 50 that facilitate the monitoring of contaminant(s) within the carbon dioxide being monitored. As shown in FIG. 2, the bottom of the housing 30 provides five external connections 50, including two fluidic connections 52a, 52b, a communication connector 54, a power connector 56, and an auxiliary data port 58. However, other embodiments of the contaminant sensor 20 may include more or fewer external connections 50, as well as connections of different types and in different positions.

The fluidic connections 52a, 52b include an intake ("IN") port 52a and an exhaust ("OUT") port 52b, which connect to the tubing/piping 18 from the delivery system 14. The intake port 52a and the exhaust port 52b connect to filter, valves, and the flow cell which houses a waveguide, discussed in detail below. In an aspect, the fluidic connections 52a, 52b can connect to an intake hose and an exhaust hose, respectively, that are connected to the delivery system 14. These ports 52a, 52b may include nipples or connectors that connect to the respective hoses/piping 18. In an aspect, it is preferable that the nipples/connectors and hoses are of different sizes to preclude cross connection. For example, the nipple/connector of the intake port 52a can be configured to connect only to the intake hose, whereas the nipple/connector of the exhaust port 52b is configured to be sized only to fit the exhaust hose of the piping 18. Further, it is preferable that the hoses/pipes 18 and all other parts exposed to the carbon dioxide be made of materials that do not leach off or absorb contaminants. This material, as discussed above, can include, but is not limited to, stainless steel, PTFE (polytetrafluoroethylene), polyethylene, or Tygon tubing. In an aspect, the ports 52a, 52b can be configured to have the piping/hosing 18 from the delivery system 14 rigidly couple to the contaminant sensor 20 in order to prevent leakage of the carbon dioxide.

The communication connector 54, labeled "CTRL" in FIG. 2, outputs real-time detection data, which includes information about the contaminants found in the carbon dioxide, including level, concentration, and contaminant makeup. The communication connection 54 can be achieved wirelessly by adding an external wireless dongle at the CTRL port, or by using an internal modem. Further, in some aspects, the contaminant sensor 20 will not have an exposed communication connector 54 in order to prevent any unauthorized electronic access to the contaminant sensor 20.

According to an aspect, the power connector 56 is configured to accept a plug-in power cable. The power cable can be a standard 110 VAC, 3-prong cable approved for use in the United States. Other power cables suitable for other countries may be utilized as well. In some embodiments of the present invention, the power cable is hardwired into the contaminant sensor 20, with the appropriate strain relief. Power can be supplied to the contaminant sensor 20 from an on-site source, or from an electrical grid. In another aspect, the power connector 56 can be configured to be connected to a removable power source, such as a battery or an external adapter. In another aspect, the contaminant sensor 20 can have an internal power source, wherein the power connector 56 is used for backup purposes. The internal power source can include, but is not limited to, a rechargeable battery, a replaceable battery, or some other means.

In an aspect, the contaminant sensor 20 can include auxiliary data ports 58, which enable additional access to sensor detection data and software. The auxiliary ports 58 can be configured to be compatible with standard electrical interfaces, including high-speed serial buses such as USB or Thunderbolt, Ethernet, Firewire, and the like. Some embodiments of the contaminant sensor 20 can include a dedicated memory stick configured to removably couple to the auxiliary data port 58. Such a memory stick can be used in a backup system to retain collected information, including part of the detection data. For example, in instances when the communication means of the contaminant sensor 20 becomes unavailable or broken, the data can still be collected and available by using a memory stick. The memory stick can be configured to connect to the contaminant sensor 20 to download data.

The auxiliary data port 58 can also be configured to provide the interface for calibration and diagnostics, as well as the uploading of new detection software and data. For example, the detection data can include the calibration information needed to keep the contaminant sensor 20 operational. The auxiliary data port 58 can be provided as a separate output from the communications connector 54 to allow a user to connect to the contaminant sensor 20 and download historical or real-time detection data without interrupting the output signal to the communications connector 54.

Figure 3:
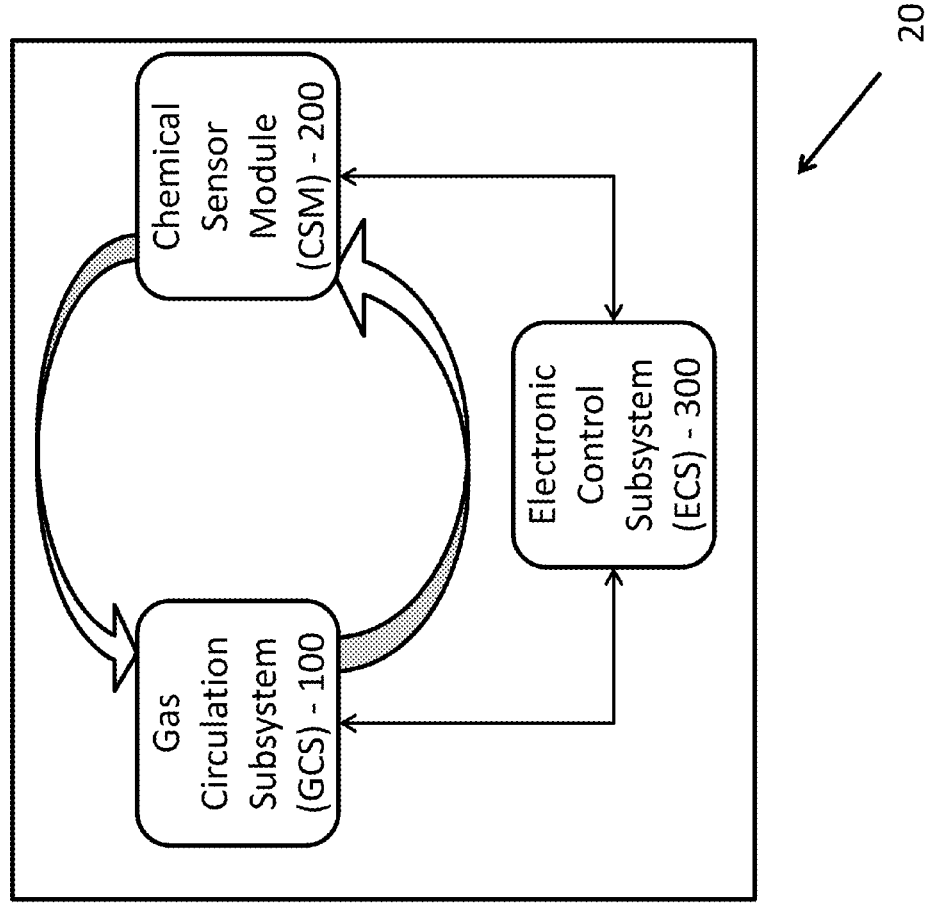
FIG. 3 is a schematic representation of the subsystems of the carbon dioxide monitoring system of FIG. 1.

As discussed above, the contaminant sensor 20 includes hardware and software components. In an aspect, the hardware components of the contaminant sensor 20 can include three interdependent subsystems organized by hardware function—not by physical location or implementation. As shown in FIG. 3, the subsystems are a Gas Circulation Subsystem (GCS) 100, which includes filters and valves that interact with all external and internal hoses (shown in FIG. 4), a chemical sensor module 200 (CSM), which includes a light source, such as a laser, waveguide, camera, and mount (shown in FIGS. 5-6) and a system controller 300, referred to herein as an electronic control subsystem 300 (ECS) to avoid confusion between the other controllers discussed above and below. The ECS 300 can be thought of as a computer contained with the contaminant sensor 20 (see FIG. 12). The ECS 300 can be configured to collect the contaminant/chemical information detected by the CSM 200 in real time, use this detection data 1407 with detection software 1406, both represented in FIG. 12, to determine the amount of a particular contaminant in the carbon dioxide. The ECS 300 can be an embedded system or single board computer which controls the GCS 100, the CSM 200, image processing from the CSM 200, data processing, the user interface 40, external connectors 50, and power conditioning. The ECS 300 provides power and commands to all electronic components of the GCS 100, and receives data from the CSM 200. The ECS 300 also outputs data to the communication connector 54 and auxiliary data connectors 58, and receives commands from the auxiliary data connector 58. In an embodiment, 110 VAC Power enters through the power connector 56 and is converted to required levels by the ECS 300.

Figure 4:
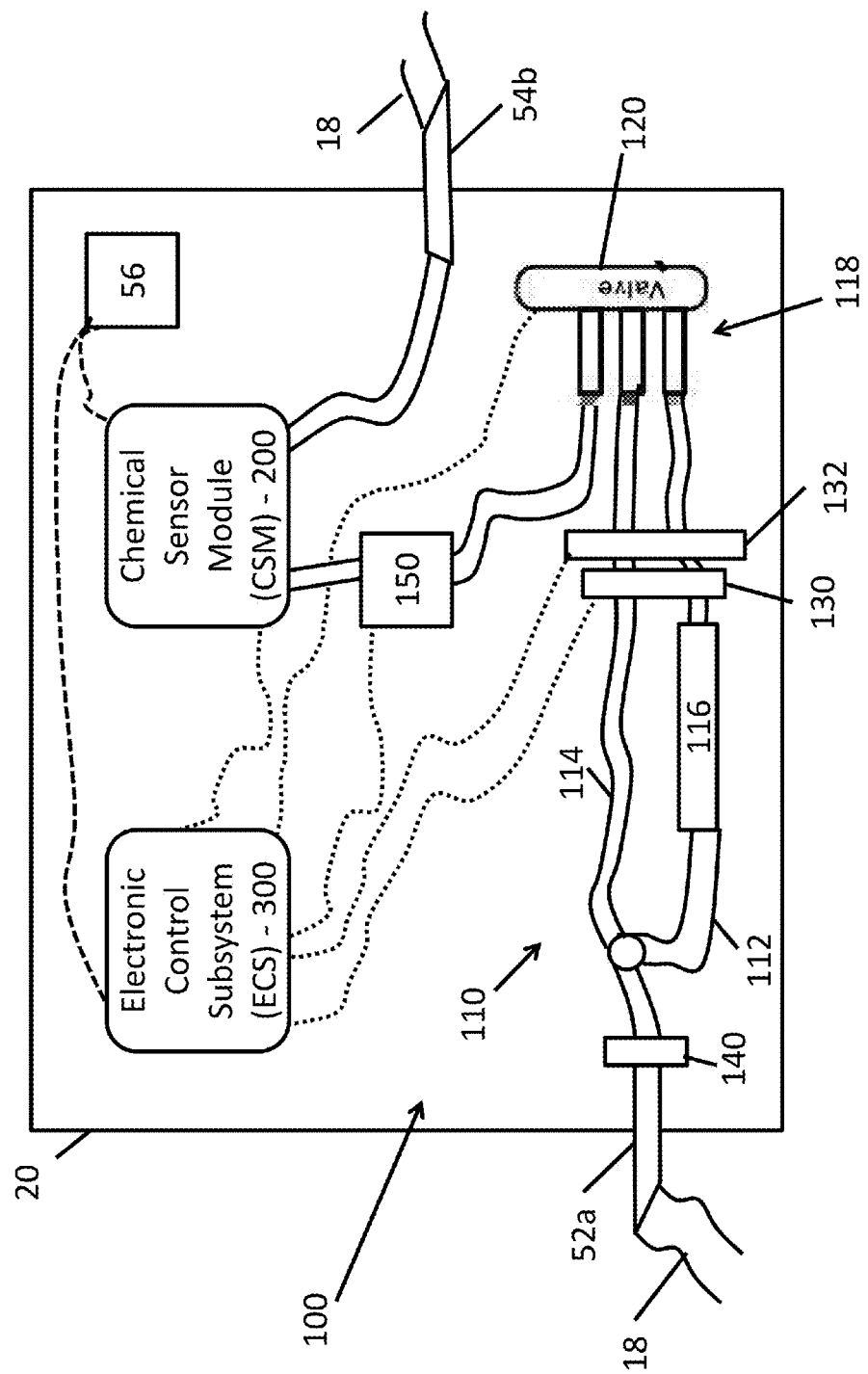
FIG. 4 is a schematic representation of the carbon dioxide monitoring system of FIG. 3.

FIG. 4 is a block diagram showing connections and flow in the GCS 100. In one embodiment, carbon dioxide enters on the left through the gas intake port 52a through at least one path 110 through the GSC 100. In an aspect, the gas intake port 52a can include a particulate filter 140. The particulate filter 140 can be configured to prevent solid matter from clogging the contaminant sensor 20. Once carbon dioxide has entered the gas intake port 52a, and gone through the particulate filter 140, the carbon dioxide can be immediately split into two paths: a filtered path 112 and an unfiltered path 114. The filtered path 112 includes the carbon dioxide going through a contaminant filter 116. The other path 114 bypasses the contaminant filter 116, resulting in the carbon dioxide being unfiltered. Both paths 112, 114 terminate in inlets 118 to a selector valve 120, which selects either the filtered carbon dioxide (i.e., the carbon dioxide that passes through the contaminant filter 116) or the unfiltered carbon dioxide to pass through to the waveguide 230, which is contained in a flow cell 220, both of which are contained in the CSM 200, discussed in more detail below. The contaminant filter 116 is configured to remove the monitored contaminants from the carbon dioxide stream of the filtered path 112, but should not affect temperature or other characteristics. The filter material may be comprised of, but is not limited to, charcoal or activated carbon. In an aspect, the contaminant filter 116 can be configured to remove various contaminants for which the contaminant sensor 20 is configured to monitor, including, but not limited to, acetaldehyde, benzene, toluene, sulfur compounds, and other VOCs including methane. In an aspect, the contaminant filter 116 filters the targeted contaminant out of the carbon dioxide without having an impact on the other characteristics of the carbon dioxide that can have an effect on the reading (e.g., humidity level, temperature, etc.). In an aspect, a single contaminant filter 116 can be used to filter out the monitored contaminants, or a series of different contaminant filters 116 can be utilized to filter the contaminants from the filtered path 112. In an aspect, the contaminant filter 116 can be monitored for replacement. The monitoring of the analyte filter 116 can be done through various sensor means, or can be done based upon the known efficiency/lifespan of the filter 116.

By having a filtered path 112 and a non-filtered path 114, the sensor 20, and more specifically the CSM 200, can self-calibrate on a regular basis to reduce sensor drift and maintain accuracy. For each sense cycle, the filtered carbon dioxide passed through the filtered path 112 is first measured to establish a zero-contaminant baseline, in order to cancel waveguide drift. The GCS 100 may also adjust the temperature of the gas being monitored. The filtered carbon dioxide path 112 and the unfiltered carbon dioxide path 114 should be balanced in terms of the flow rate, pressure drop, temperature, and the travel time for carbon dioxide through the respective path 112, 114. In another aspect, to further ensure accurate measurement, the GCS 100 can utilize a temperature sensor 130 and a temperature controlling mechanism 132 (e.g., a fan or heating coil) to regulate temperatures of the carbon dioxide passing through the filtered path 112 and the unfiltered path 114.

In an aspect, the sensor 20, and more specifically the GCS 100, is configured to utilize the pressure supplied by the carbon dioxide delivery system 14 in order to control the flow of the carbon dioxide through the different paths 112, 114. However, in an aspect, an optional pump 150 can be provided. In an aspect, the pump 150 can control the flow of the carbon dioxide through the GCS 100 to the CSM 200. The pump 150, whose location in the stream can change (i.e., the pump 150 can be external to or can be contained within the contaminant sensor 20), either pushes or pulls the carbon dioxide through the contaminant sensor 20, including to the CSM 200, for the monitoring, identification, and measurement of the contaminant.

In an aspect, the GCS 100 can be configured to assist in measuring/identifying/monitoring the contaminants of interest. For example, the GSC 300 can be configured to include filters 140 configured to remove non-target contaminants, as well as contaminants/particulates that can interfere with the monitoring. In such aspects, the filters 140 can be configured to engage the carbon dioxide at the inlet port 52a. Similar to the contaminant filters 116, these filters 140 can be monitored for efficiency.

Once the detection steps, discussed in detail below, have been performed, the carbon dioxide can exit the CSM 200 and pass through the exhaust port 52b where the carbon dioxide can travel onto the target 16. In an alternative embodiment, the contaminant sensor 20 contains two selector valves 120, and carbon dioxide is continually pushed through both paths 112, 114 so that there is no latency between the environmental characteristics of the carbon dioxide in each path 112, 114. Carbon dioxide from the path not being pushed through the CSM 200 bypasses the CSM 200 and is coupled with carbon dioxide coming out of the CSM 200 to be exhausted through the exhaust port 52b.

In an aspect, while it is important for the inlet and exhaust ports 52a, 52b to remain unblocked, the carbon dioxide monitoring system 10, and more specifically the GCS 100, can be configured to operate without causing damage to itself if either port 52a, 52b becomes blocked for an indefinite period of time. In an aspect, a particulate filter can be placed in proximity to the intake port 52a. In another aspect, a pressure sensor can be used to measure the pressure occurring along the different carbon dioxide paths 112, 114. If the pressure sensor finds that a path is experiencing pressure outside of allowable ranges, the contaminant sensor 20 can be configured to shut off, or report the results to the system controller/control electronics 300. Further, the contaminant filter 116 does not have unlimited capacity and should be replaced as a part of normal maintenance.

FIGS. 5, 6, 6a, and 6b illustrate components of the chemical sensor module (CSM) 200. The CSM 200 utilizes optical interferometry through a comparison of optical paths to sense the amount and makeup of contaminants in carbon dioxide. The channels within the interferometer create separate optical paths from which interference patterns can be generated. While the preferred embodiment of the present invention utilizes a Mach-Zehnder interferometer, other optical interferometers, including, but not limited to, Michelson, Fabry-Perot, Twyman-Green, Sagnac, Rayleigh, and Jamin interferometers can be used. The interferometer includes at least one sensing channels coated with a polymer that selectively changes its index of refraction when exposed to contaminants found in the carbon dioxide. Thus, an optical path will be changed by the presence of the contaminant, while a separate reference channel will be unaffected by the contaminant. This change to the optical path creates a change in the interference pattern as the polymer is exposed to the chemical, allowing an almost instantaneous reading.

Figure 5:
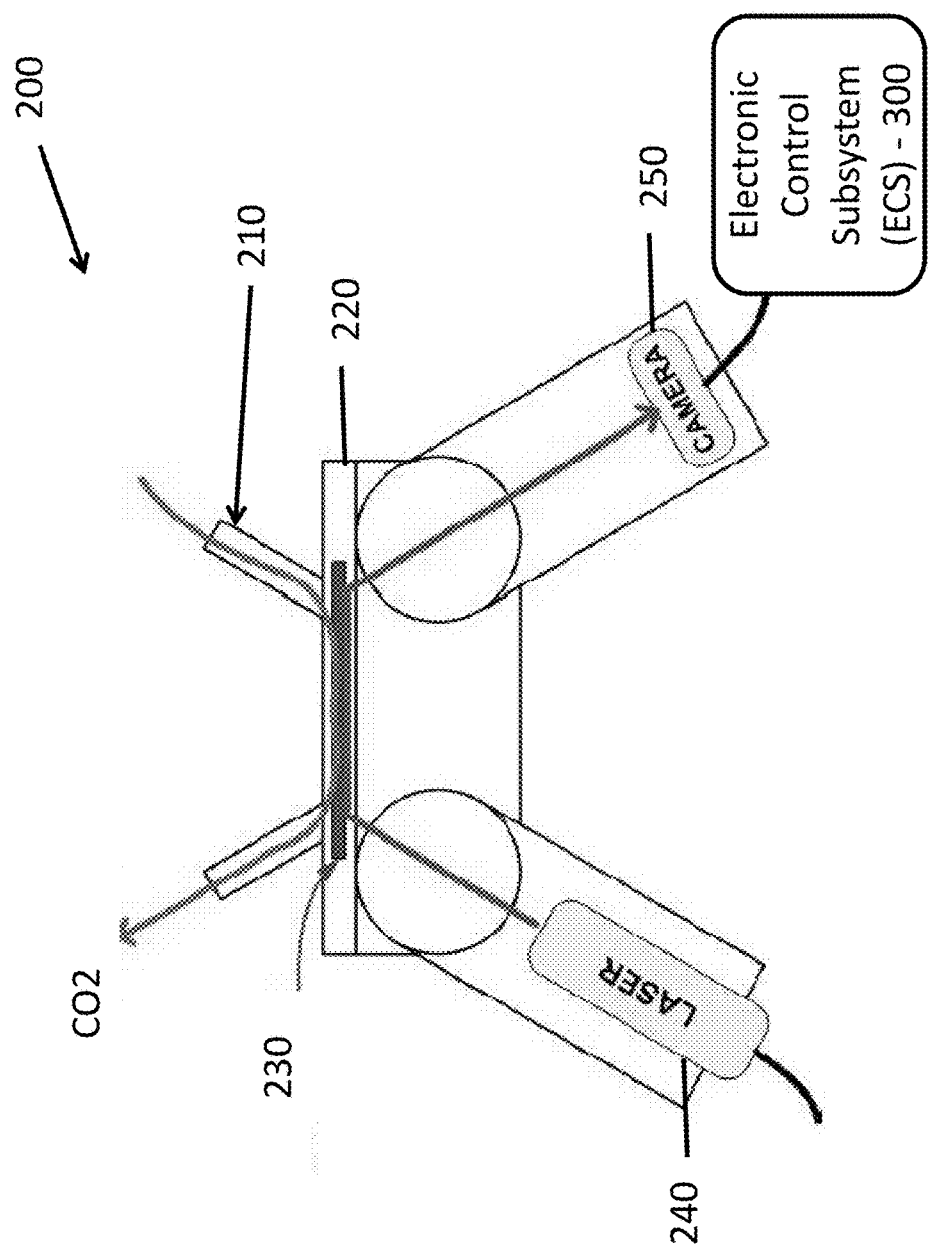
FIG. 5 is a cross-sectional side schematic view of the chemical sensor module of the carbon dioxide monitoring system according to one embodiment of the present invention.

Carbon dioxide, labeled as "carbon dioxide flow" at the top of FIG. 5, is pushed in from the right through an inlet tube 210, and passes through a sealed chamber (i.e. flow cell) 220 over a waveguide 230. At the same time, a low power laser 240, which in one embodiment has a center wavelength of 670 nm, radiates a beam of monochromatic light into the waveguide 230. Interference patterns are displayed on a camera 250 or otherwise captured by another form of optical detector 250, at the output side of the CSM 200. For example, one embodiment of the present invention utilizes a UI-1542LE-M model camera from IDS Imaging.

Figure 6:
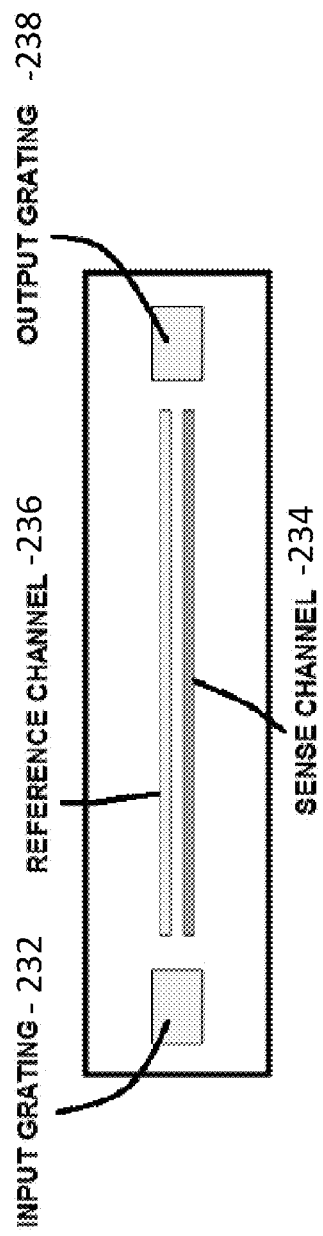
FIG. 6 is a schematic top view of a waveguide of FIG. 5.

The waveguide 230, shown from a top view in FIG. 6, consists of an input grating 232, one or more pairs of parallel channels—sense 234 and reference 236—and one or more output gratings 238. The waveguide 230 is a stacked thin film structure with a base of optical glass, a thin core layer of a higher-index material, and an upper cladding layer into which are etched the long, narrow channels. In an aspect, the waveguide 230 can be comprised of, but is not limited to, fused silica glass, quartz glass, silicon, and tantalum pentoxide.

Figure 6B:
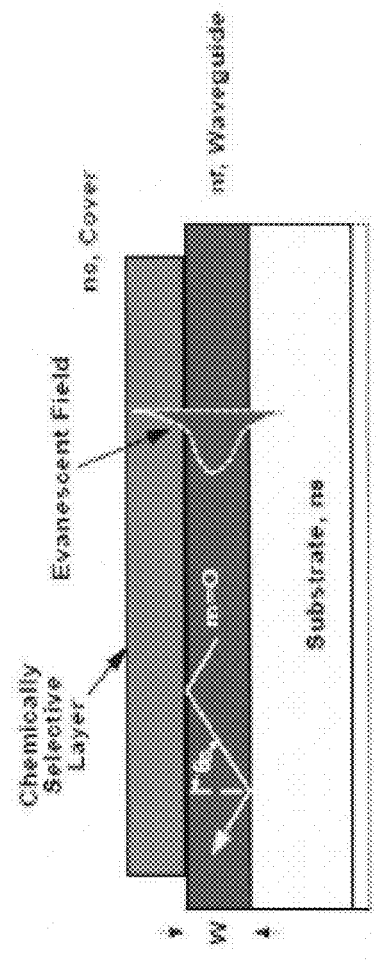
FIG. 6b, is a schematic representation of a single mode waveguide with buried evanescent field according to an aspect.
Figure 6A:
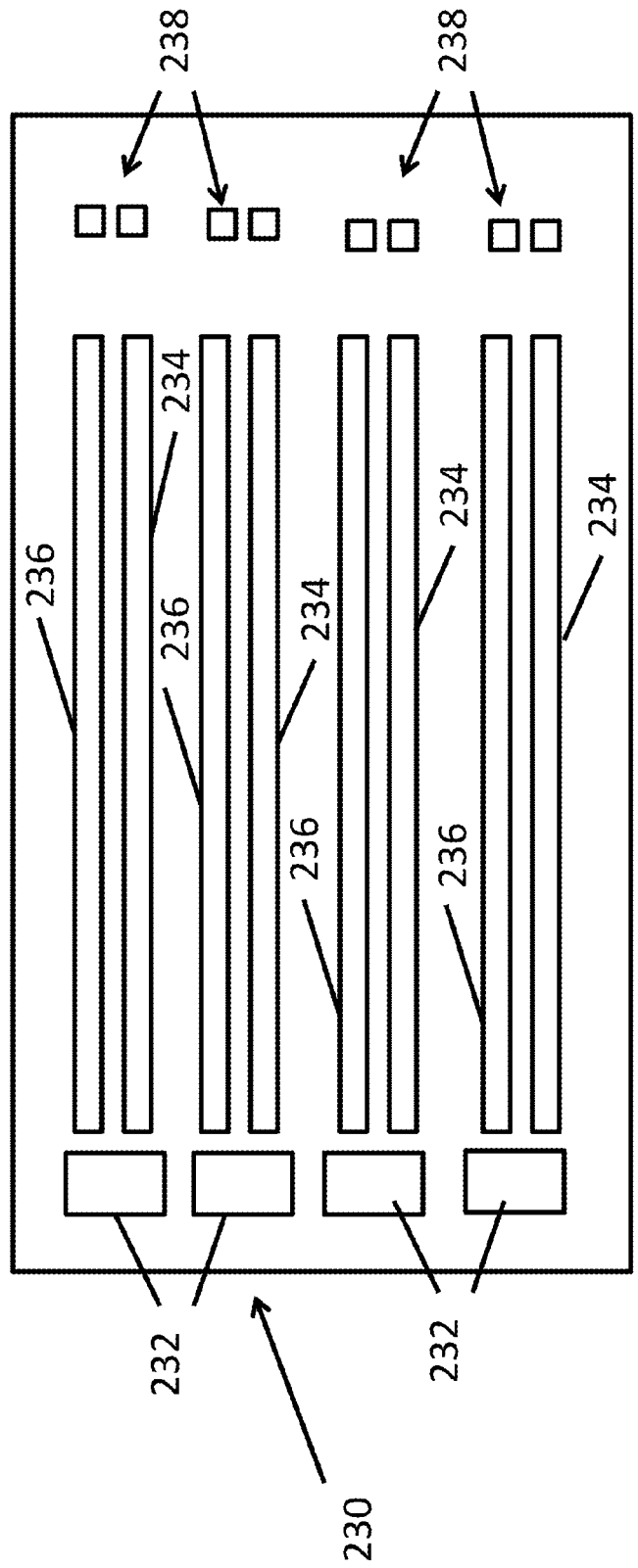
FIG. 6a is a top view of a waveguide with four separate channel pairs.

FIG. 6a is a top view of a waveguide 230 having four pairs of sense 234 and reference 236 channels. The laser's light travels down the optical paths associated with the sensor channel and the reference channel by entering the input grating from the bottom of the waveguide 230, with the light being refracted to travel down the length of the channels (left to right in FIGS. 5 and 6).

Each sense channel 234 is filled with a chemically sensitive polymer, whose index of refraction changes in proportion to contaminant adsorption, causing the speed of light in that polymer to change correspondingly. A portion of the light (its evanescent field, as shown in FIG. 6b) travels through the polymer coating that has been applied to the surface of each sense channel. The interference pattern generated by the optical interaction of light from each channel pair of the optical paths is captured by the optical detector 250. The phase shift of this interference pattern, which is proportional to the concentration of the target contaminant, is determined using a processor running image processing algorithms.

For example, the polymers that can be used to identify the type(s), concentration, and composition of contaminants in the carbon dioxide include, but are not limited to, PVP, PVA, PHEM, PVB, PTBrS, PVF, PEI, PVPy, PHPC, PBIBMA, TAF, PDMA, PMOS, PSSA, PVPK, and PIB. The types of contaminants that can be identified include, but are not limited to, acetaldehyde, benzene, toluene, sulfur compounds, and other VOCs including methane.

In other embodiments of the invention, other coatings and thicknesses can be used. The reference channel 236 is covered so as to not be affected by the polymer coating (i.e., it does not react to the contaminants found in the carbon dioxide). The speed of light in each channel 234, 236 will be different to a degree proportional to the amount of contaminants in the carbon dioxide sample.

After exiting the right-hand side of each channel 234, 236, both light beams are again refracted and combined by the output grating, projecting an interference pattern onto the surface of the camera 250 or other form of optical detector. In one embodiment, the p[toca; detector 250 is a charge-coupled device (CCD). In an alternative embodiment, the optical detector 250 is a complementary metal-oxide-semiconductor (CMOS) sensor. If contaminants are present, the sense and reference light waves will travel at different speeds, and one will arrive at the output grating 238 before the other, causing a phase shift and a change in the interference pattern on the camera 250 that is proportional to contaminant concentration. The CE 300 analyzes the camera image and measures the change in the interference pattern to determine the concentration and identification of contaminants using calibration coefficients associated with the contaminant sensor 20. These coefficients may be updated through various means as well.

While FIG. 6 depicts a single pair of channels on the waveguide, waveguides may also contain multiple channel pairs (as shown in FIG. 6a), each with the same or different sense polymers, to sense multiple contaminants in the carbon dioxide sample, or to increase specificity and reliability. The ratio of the adsorption responses of a given contaminant to different polymers is often highly unique, and can be used to determine the identity of a contaminant, or the composition of a contaminant mixture. The addition of even more sense channels 234 with different polymers, and thus more polymer pairs, to a waveguide 230 allows for more ratios to be measured and an increasing number of contaminants in a complex mixture to be identified and quantified. A signature of response ratios across the collection of polymer pairs on the waveguide 230 can be established for any contaminant mixture. The addition of more sense channels also increases the ability of the sensor to differentiate contaminant targets from other "interferent" compounds, which do not need to be detected but could otherwise be mistaken by the sensor for target contaminants. Interferents can also be discerned through signal processing, if their transient response or signature of response ratios is different from those of the contaminant targets.

The ECS 300 is resident in the sensor housing 30 and is not accessible to the user except functionally via the user interface 40 or external connectors 50. The ECS 300 includes the power control system of the contaminant sensor 20. It is preferred that the power control system include a current monitor to detect off-nominal conditions, discussed in more detail below. The ECS 300 includes on-board memory. It is preferred that the memory of the ECS 300 be of a nonvolatile type and provide enough on-board memory to store an extended history of readings, consistent with application requirements, at the shortest reading interval, which can be set by the user. In the preferred embodiment, the memory is erased on a first-in, first-out basis when the memory becomes full. An additional 16 k of user-defined identification data is also provided, as well as at least 512 k to maintain a System Log file. The preferred embodiment of the ECS 300 includes a real-time clock (RTC) which continues to track time even when the system is powered down. It is preferred that the RTC shall maintain an accuracy of better than ±6 hours per year for up to three years.

In an aspect, the ECS 300 is configured to carry out the following functions: control the GCS 100; control the CSM 200; process images received from the CSM 200, including image cropping; determine an appropriate measurement zone; determine the interference pattern period within that zone; interpret interference pattern data and correlate with calibration data to obtain a contaminant concentration reading; control the user interface 40; interface with the communication connector 54 and auxiliary outputs 58; interface with the user via the user interface 40 to set options and conduct maintenance; manage power input to the system 10; detect system faults and respond to them; save contaminant concentration data to a time-stamped data file; save significant events to a System Log; and detect and react to exceptions and errors. These functions can be implemented and executed using various coding languages, like C and variations, or through various application layer software, including, but not limited to, LabVIEW® software from National Instruments.

In an aspect, the ECS 300 can be configured to determine if a contaminant is present, and if so, the contaminant concentration from the information provided and captured by the CSM 200. In an aspect, the ECS 300 can determine whether a contaminant is present and if so the concentration of the contaminant through a method 600 as illustrated in FIG. 7. As shown in FIG. 7, the ECS 300 will first determine if the contaminant is present (step 610), determine the rate of change of the presence of the contaminant as the contaminant sensor 20 is exposed to the carbon dioxide (step 620), correlating the change over the time period with calibration data to obtain an carbon dioxide concentration reading (step 630), and processing the contaminant concentration reading to eliminate noise and other potential faulty data (step 640). In an exemplary aspect, the ECS 300 can utilize a detection application 406 to perform the method 600.

The ECS 300 can determine whether or not the contaminant is present by examining signals generated from the CSM 200 (step 610). For example, if the CSM 200 passes along signals that indicate a change, the ECS 300 will determine that the contaminant is present. In other aspects, the CSM 200 can be configured to provide a separate signal upon the detection of the targeted contaminant.

Once the ECS 300, via the detection application 506, discussed in more detail below, determines the contaminant is present, the ECS 300 can determine the change in the amount of the contaminant exposed to the CSM 200 over a given time period (step 620). In an aspect, the ECS 300 can determine this information based upon the signals generated by the CSM 200. In an aspect, the ECS 300 can utilize processing algorithms to determine the change from the signals.

Upon determining the change in the amount of contaminant (step 620), the ECS 300 can then correlate the change data with calibration data to obtain a contaminant concentration reading (step 630). In an exemplary aspect, the change data can be multiplied by a calibration coefficient to determine the contaminant concentration reading.

Once the contaminant concentration reading is determined, the ECS 300 can process the concentration reading to eliminate noise and other potential faulty data (step 640). This can be done by using weighted averaging algorithms or other signal processing techniques. In addition, other environmental conditions can be considered as well to eliminate faulty data. For example, the contaminant concentration reading can be adjusted according to the current humidity level. Such information can be obtained through humidity sensors.

The ECS 300 controls the operation of the carbon dioxide monitoring system 10. The ECS 300 is configured to provide simple operations for a user. As such, in the preferred embodiments of the system, the contaminant sensor 20 has a limited number of modes: the Measurement Mode, the Standby Mode, the System Error Mode, the Maintenance Mode, and the Calibration and Diagnostic Mode. While it is preferred that the contaminant sensor 20 be limited to these five modes, other embodiments may include more optional modes, different modes, or fewer modes.

Figure 8:
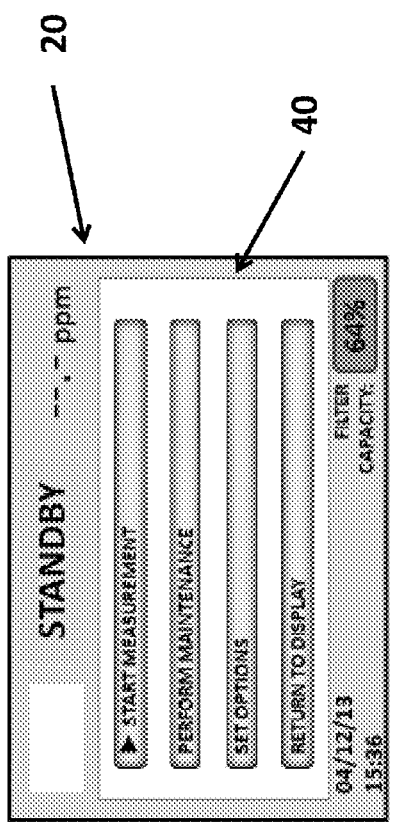
FIGS. 8-10 are representations of the display of the real-time contaminant sensor of FIG. 1.
Figure 9:
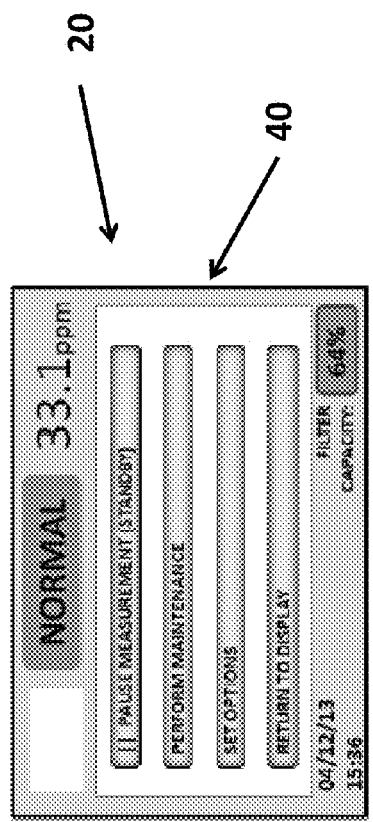

The screen illustrations in this section are provided to give an overview of each screen's contents. They are not meant to suggest specific layout or artwork for the screen. The screens shown are meant to correspond to the LCD Touchscreen area shown in FIG. 2. As shown in FIGS. 8 and 9, the display includes certain information provided to the user, including the status of which mode the contaminant sensor 20 is presently operating, and any corresponding readings. For example, the display can include a measurement status indicator. As shown in FIG. 8, the measurement status indicator shows that the system is in Standby mode. In Standby mode, the contaminant sensor 20 is not operational, and displays "STANDBY" on its screen.

When in the Measurement Mode, the contaminant sensor 20 measures (on a near-continuous basis), displays, and records contaminant levels, presence, and compositions according to system presets. As shown in FIG. 9, the measurement status indicator shows that the carbon dioxide monitoring system 10 is in the MEASUREMENT mode, displaying a "NORMAL" with a green background that indicates the system 10 is presently taking measurements, and the last measurement was within the Normal threshold set by the user. When the contaminant sensor 20 finds that a last measurement of contaminant is above a Caution threshold set by the user, a "CAUTION" with a yellow background measurement status indicator is displayed. Likewise, when the contaminant sensor 20 finds that a last measurement of contaminant is above a user-set Warning threshold, a "WARNING" with a red background measurement status indicator is displayed. Other embodiments may use descriptive words other than "Normal," "Caution," or "Warning." Graphs showing results for more than one contaminant may be shown on the screen at one time, or the display may include a separate provision to cycle the display through each separate contaminant being monitored by the sensor.

In addition to the measurement status indicator, the display 40 includes a last measurement numerical indicator, a data/time display, and the filter capacity display. The numerical indicator indicates the last contaminant reading, or set of readings, taken. In Standby mode, this indicator reads "--.-". Further, it is preferable that the numerical indicator display the amount with varying precision depending upon which contaminant's data is being displayed. For example, the precision for the display of acetaldehyde concentrations may be 50 ppb, while the precision for benzene may be 5 ppb. The date/time display shows the present date and time, with minute precision, and is user adjustable in the preferred embodiment. Also in the preferred embodiment, the date/time display adjusts for daylight savings time (US and Europe) and leap years. Lastly, the filter capacity display indicates the status, present capacity, or remaining life of the contaminant filter(s) 116. In the preferred embodiment, the processor keeps track of the total amount of contaminants to which the filter(s) 116 has been exposed, as well as the time of exposure, and calculates remaining filter life. In one manifestation, the numerical indicator is green for high capacity, transitions to yellow at a lower value, and then to red at a still lower value. In another it may read like an automobile's fuel gauge, full to empty. When the filter capacity is at zero, the contaminant sensor will no longer take readings, and displays a "change filter" message. The default threshold values for the indicator color changes can be changed based upon the user's preference. In the preferred embodiment, the number is automatically reset to its maximum each time the user goes through Maintenance mode. In some embodiments of the present invention, the filter capacity display will notify the user when a new filter 116 has been installed improperly.

Referring to FIGS. 8 and 9, the display includes Main Menu Controls. The Main Menu Controls as displayed by the preferred embodiment include a Start/Pause Measurement button, a Performance Maintenance button, a Set Options button, and a Return to Display button.

Figure 10:
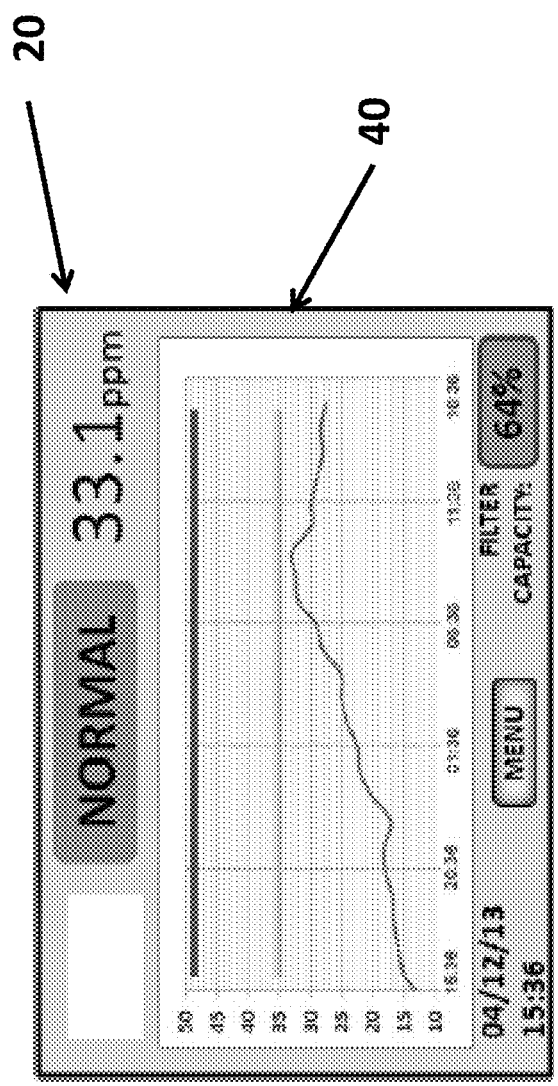

The Start/Pause Measurement button toggles between 'Start' and 'Pause' measurement. When pushed from Standby mode, it places the carbon dioxide monitoring system 10 in Measurement mode. When pushed from Measurement mode, it places the carbon dioxide monitoring system 10 in Standby mode. The Perform Maintenance button launches Maintenance mode, described in more detail below. The Set Options button opens a lower level of menus and keypad displays that allow the user to change system options. The Return to Display button returns to the graphical display of historical measured contaminant levels, as shown in FIG. 10. When in Standby Mode, the display is static and shows the most recent readings. When in Measurement Mode, the display is dynamic and continues to update. The Measurement Status Indicator, Last Measurement Numerical Indicator, Filter Capacity Indicator, and Date/Time Display continue to be displayed, independent of whether the graphical display or the menu is included in the embodiment.

As discussed above, the Graphical Display is initiated from the "Return to Display" button on the Main Menu. FIG. 10 illustrates the Graphical Display in Measurement Mode. As shown, the only control on the Graphical Display screen is the "Menu" button, which returns to the Main Menu (while remaining in either Standby or Measurement Mode). In other embodiments of the present invention, other buttons may be included on the Graphical Display.

The Graphical Display shows historical contaminant readings. In Measurement Mode, it updates in real time. In Standby Mode, it shows the most recent readings. The 'x' axis is time; 'y' axis is contaminant level in ppm (parts-per-million) or ppb (parts-per-billion). Both axes are user-adjustable and can auto-scale, as necessary and as desired, to accommodate the data. Yellow and red lines indicate the user-adjusted "Caution" and "Warning" thresholds, respectively. Date range limits on the display can be set by the user. Readings for multiple contaminants may be displayed simultaneously, either on separate charts, or combined in a single same chart.

The parameters are displayed as a series of points connected by straight lines, during periods where the contaminant sensor was in Measurement Mode. If the unit was placed in Standby Mode at any point during the time interval displayed, values during those durations are not displayed on the Display, appearing as gaps in the line. While FIG. 10 shows the display illustrating the numbers using a traditional x and y axis that correspond to time and contaminant levels, other types of graphical representations may be used in other embodiments, including, but not limited to, bar charts with min, max, and current levels, or pie charts.

The system enters Measurement mode: (a) when "Start Measurement" is selected from the Main Menu; or (b) when the system returns from System Error Mode, if Measurement Mode was the last known mode.

Figure 11:
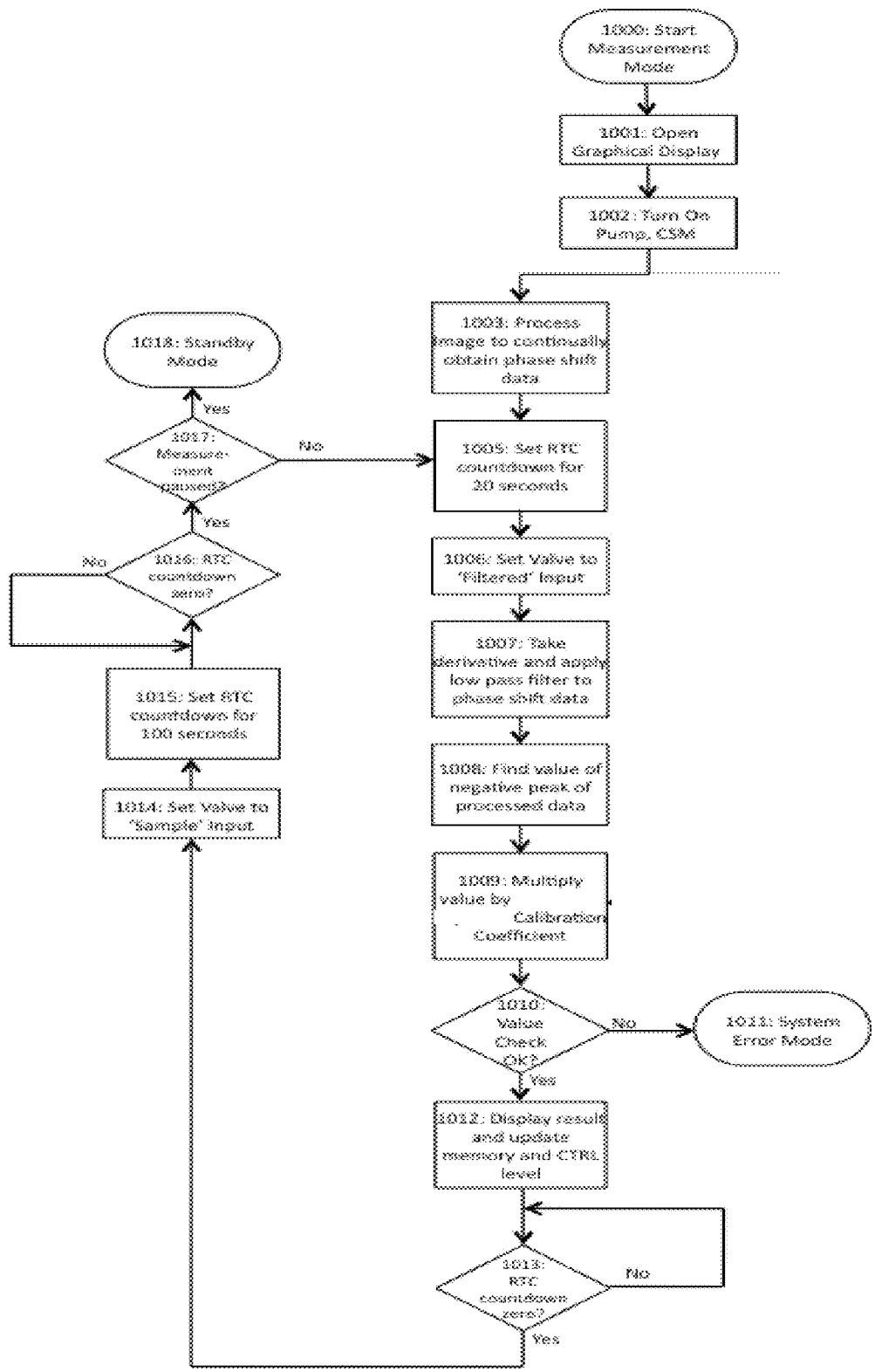
FIGS. 11-12 are flow diagrams of methods performed by a carbon dioxide monitoring system according to an aspect of the present invention.

In Measurement Mode the Touchscreen 40 displays the Graphical Display as in FIG. 10. As always, the user may toggle between the Graphical Display and the Main Menu without leaving Measurement Mode. The contaminant sensor 20 continuously takes contaminant level readings at the time interval specified by the Measurement Interval parameter, according to the behavioral flow shown in FIG. 11.

When the Measurement Mode is started (1000), the graphical display is changed (1001) to show something similar to that presented in FIG. 10. The pump 100, laser 240, and camera 250 are turned on and initialized as appropriate (1002). Using image processing algorithms, which in one embodiment include the use of Fourier transforms, the carbon dioxide monitoring system 10, for each interferometer (i.e., the input grating 232, sense channel 234, reference channel 236, and output grating 238) on the waveguide 230 or set of waveguides 230 in the sensor 20, begins tracking the phase shift that occurs in the interference pattern detected by the camera 250 (1003). Using the real-time clock, a counter is set (1005) for a duration (20 seconds for the preferred embodiment, but the duration can vary depending on the application in which the carbon dioxide monitoring system is utilized), and the selector valve 120 is switched (1006) so that carbon dioxide having been filtered by the contaminant filter 116 travels through the flow cell 220 and over the waveguide 230. Phase shift data obtained by the image processing algorithms for each interferometer is further processed. According to one embodiment, the carbon dioxide monitoring system 10 first takes the derivative (or slope) of the data, and then "low-pass" filters the derivative data (1007). The maximum negative value of this processed data is then found (1008). Since the speed of the chemical adsorption and desorption of the contaminant responsive polymer coating is proportional to the presence and concentration of a specific contaminant in the sample, the derivative approach can be used. This approach can, in some embodiments, improve sensing speed and preserve filter capacity. The value found in (1008) is then multiplied by a calibration coefficient (1009). The calibration coefficient can be provided at the time of installation of the waveguide 230 in the contaminant sensor 20, and can be updated when needed at field calibration events. If the value obtained is within a reasonable range (which can be application dependent and defined at installation or by customers defining the out-of-bound reading levels) and not dramatically different from the last measurement (stored locally within the contaminant sensor 20 via the ECS 300) (1010), and if no other errors or failures are detected in the contaminant sensor 20, the value is then logged and passed along, or stored (1012). If the value is found not to be within the appropriate range, or an error is reported, the contaminant sensor 20 enters System Error Mode (1011). Then, the carbon dioxide monitoring system 10 waits until the countdown has reached zero (1013) and, when this has occurred, the selector valve 120 of the GCS 100 is switched so that the carbon dioxide is passed unfiltered (via the unfiltered path 114) through the flow cell 220 to the waveguide 230 (1014). The countdown clock is then reset (in the preferred embodiment, the clock is reset to 100 seconds) (1015), allowing the waveguide 230, and the coatings on the sense channel 234 and reference channel 236, to adsorb and/or react to contaminant(s) from the carbon dioxide source. When the countdown again reaches zero (1016) and, assuming that the contaminant sensor 20 has not been asked to pause or standby (1017), the contaminant sensor 20 then resets the countdown and switches back to the filtered state (1005 and 1006). The carbon dioxide monitoring system 10 exits Measurement mode when: (a) the user selects "Pause Measurement Mode" from the Main menu; (b) a System Error occurs, or (c) the system is powered down.

The contaminant sensor 20 enters Standby Mode when: (a) the system is powered up; (b) the user selects "Pause Measurement" from the Main Menu, or; (c) the system recovers from a System Error and the last state before the error was Standby Mode. FIG. 8 illustrates the Touchscreen in Standby Mode, when the Main Menu is being displayed. The Status Indicator is yellow, and reads "STANDBY". The Numerical Indicator reads "--.- ppm". The user may toggle between the Main Menu and the Graphical Display by hitting the "Return to Display" or "Menu" buttons. When the Graphical Display is shown during Standby mode, only historical data is presented, with the time intervals during which the system is in standby having no data appearing as gaps in the curve. In one embodiment of the present invention, if the user invokes Standby mode while the contaminant sensor is taking a measurement, the contaminant sensor interrupts the measurement, and then enters Standby Mode.

In Standby mode, the carbon dioxide monitoring system 10 is configured as follows: selector valve 120 set to "Sense" (unfiltered) input (i.e., from unfiltered path 114), to potentially minimize flow through the contaminant filter 116; the CSM laser 240 and camera 250 are set to off; and the communication output 54 holds a 'no data' reading.

The contaminant sensor 20 enters System Error mode when it encounters certain error conditions. In some embodiments of the present invention, the System Error Mode is identical to Standby Mode, except that it is initiated by certain System Errors that require measurements to stop in order to prevent possible damage to the contaminant sensor 20 or the reporting of 'junk' data. In System Error Mode, the Status Indicator flashes red and reads "SYSTEM ERROR".

The contaminant sensor 20 generally exits System Error Mode, and returns to the last saved mode, when the error condition is corrected, either automatically or by user action. The System Log records time and date for entry into, and exit from, System Error mode.

Figure 12:
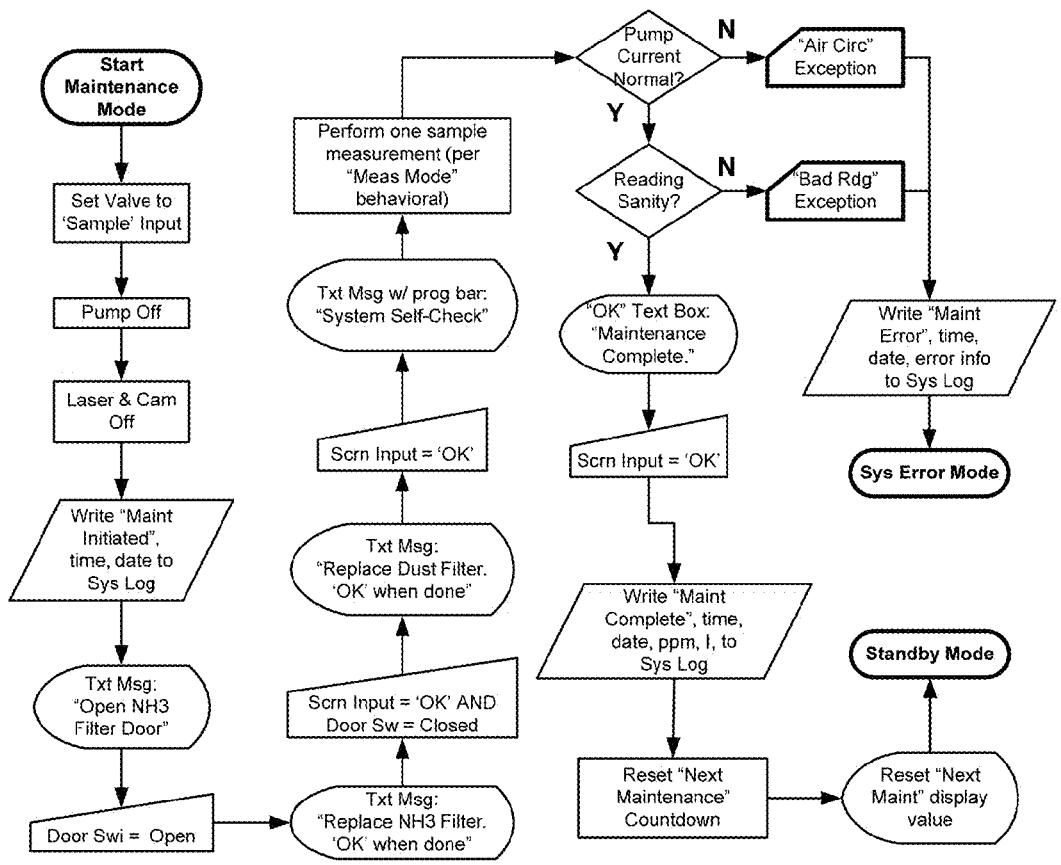

Maintenance mode places the system in a safe state and guides the user through maintenance actions. Maintenance on the carbon dioxide monitoring system 10 is intended to be carried out on a prescribed regular basis, but can be performed any time the user desires. FIG. 12 illustrates system behavior in Maintenance Mode. The User enters Maintenance mode by selecting "Perform Maintenance" from the main menu. The contaminant sensor configures the system as if in Standby Mode. A series of instructions on the Touchscreen 40 guides the user through the maintenance steps, and the contaminant sensor 20 performs several self-tests to ensure maintenance was carried out properly. The screen messages may include graphics that illustrate the task to be performed. The contaminant System Log records the start and end time/date of each maintenance.

The carbon dioxide monitoring system 10 may incorporate a maintenance countdown, which alerts the user to when the system 10 needs regularly scheduled maintenance. In addition to keeping a 'maintenance countdown', the carbon dioxide monitoring system 10 may keep a separate 'Replacement Countdown', and shall alert the user via a Touchscreen text message, shown on the user interface 40, when a replacement waveguide 230, or filter 116, is due.

Calibration and Diagnostic mode facilitates calibrating the unit and performing certain diagnostics. The user can initiate Calibration and Diagnostic mode by connecting a computer to the auxiliary port 58 and running a Calibration & Diagnostic application from the computer. The application calibrates the contaminant sensor 20 by exposing the contaminant sensor 20, and more specifically the filters 116 and CSM 200 to a test fixture containing known levels of contaminants mixed with carbon dioxide or another carrier gas, as verified by a reliable, high-precision reference sensor. The ECS 300 may be configured to guide the operator through the calibration steps, and generate appropriate calibration coefficients, based on formulas and/or lookup tables created during product development. Calibration coefficients are stored locally on the contaminant sensor 20, via the ECS 300, as well as in a global database that references calibration coefficients to device serial number and date. Calibration coefficients are preferred to remain valid for at least three years, with no updates.

The calibration application will also load identifying data into the local memory found in the ECS 300 of the sensor 20, as well as the global database. Identifying data includes device hardware revision, firmware revision, serial number, date of manufacture, CSM serial number, and Waveguide Serial Number, with space reserved for user-defined data. Other identifying data may be included as well.

The "Cal & Diagnostic" application also has the ability to retrieve, store, and display real-time diagnostic data from the contaminant sensor, to assist in troubleshooting and understanding system behavior. Parameters may include, but are not limited to, total current draw, CSM current draw, CRC scan results, measurement history, system log, raw image data, and manual control of various subsystems.

Selecting "Set Options" from the Main Menu opens a new menu with a number of options available to the user. These include "Caution" and/or "Warning" thresholds whose levels, within certain application-specific ranges, can be adjusted by the user.

As discussed above, the carbon dioxide monitoring system 10 may include a USB memory stick containing a simple application to be installed on a computer for downloading and displaying data from the contaminant sensor 20. An installation program may guide the user through the process. To download data from the contaminant sensor 20, the user connects the memory stick to the auxiliary port 58 of the sensor 20, waits for a "data download complete" message on the touchscreen, then removes the memory stick and connects the memory stick to the computer. Connection and data download can take place in any contaminant sensor mode, without interrupting the contaminant sensor 20 measurements or other functions. A simple interface will allow the user to: view date ranges available for download; select a date range and download the data for import to a program such as Microsoft Excel or other spreadsheet applications; display the data graphically for a selected date range; and/or download a copy of the System Log.

If the computer on which the data and USB memory stick currently reside is connected to the Internet, the application will, with user's permission, connect to a designated website and check for available software upgrades. If one is available, the application will download and install it to the memory stick. When the memory stick is inserted into the contaminant sensor again, it will upgrade the system software. If the contaminant sensor 20 is in Measurement mode, the application will complete the present measurement and place the system in Standby mode during upgrade, then automatically return the system to Measurement mode. The ECS 300 may also be upgraded directly if the sensor 20 is connected to the Internet.

The ECS 300 of the contaminant sensor 20 can maintain a System Log for historical and diagnostic purposes according to one embodiment of the present invention. The System log shall be available for download, and is viewable from the Options screen. It can contain time-stamped records of all significant system events. The timestamp shall be independent of the user's clock setting. Examples of 'significant system events' are: Maintenance start/stop times; System Errors; Start/Stop Measurement Mode; User Data Downloads; Options Changes by User; and Power-ups.

The control firmware of the ECS 300 of the contaminant sensor 20 is configured to handle exceptions and off-normal events during its operation. These events will not cause system instability, hardware damage, or an unsafe situation. Exceptions are normally handled by error messaging prompting the user to take action.

In other embodiments of the present invention, the location and association of the components of the carbon dioxide monitoring system 10 may vary from what is described above. For example, in one embodiment of the present invention, the various valves 120 and hoses 18 can be exposed, or be contained within the housing 30 of the contaminant sensor 20.

Figure 13:
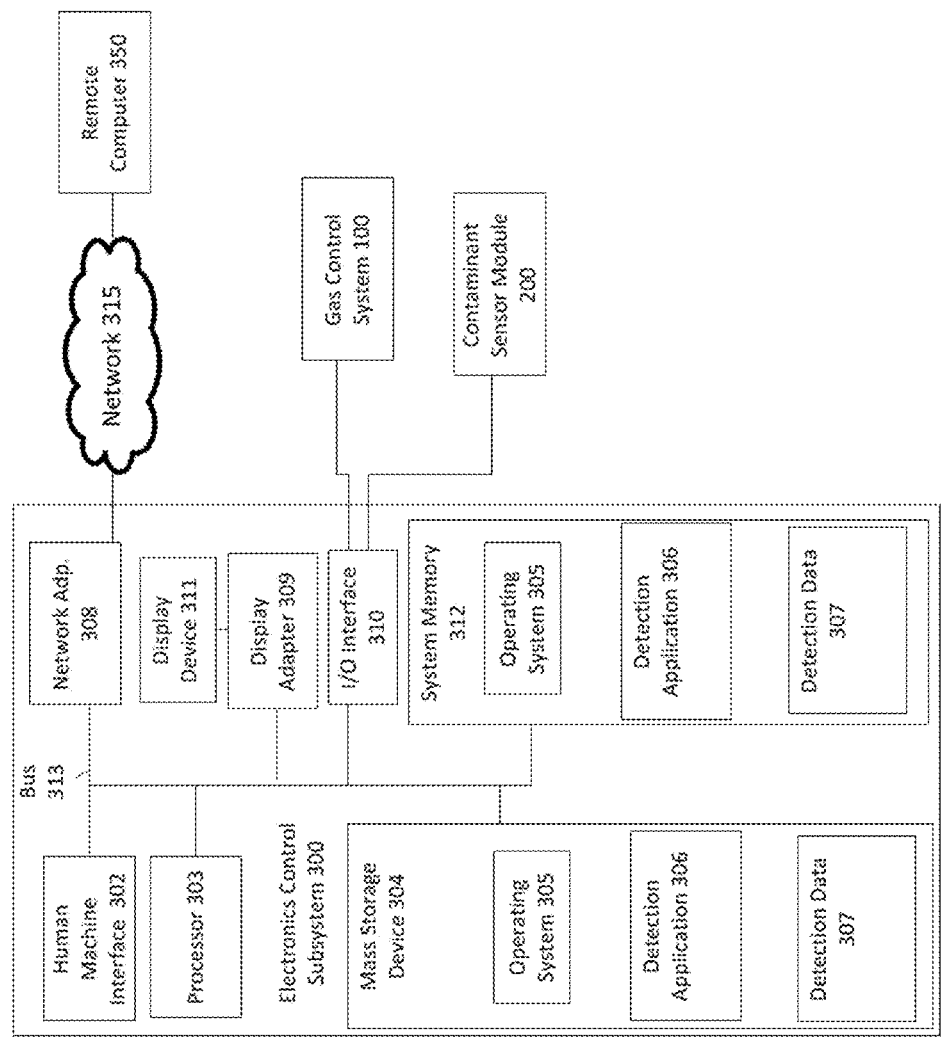
FIG. 13 is a block diagram of a control electronics system according to an aspect of the present invention.

FIG. 13 is a block diagram illustrating an exemplary operating environment for performing the disclosed methods. This exemplary operating environment is only an example of an operating environment and is not intended to suggest any limitation as to the scope of use or functionality of operating environment architecture. Neither should the operating environment be interpreted as having any dependency or requirement relating to any one or combination of components illustrated in the exemplary operating environment.

The present methods and systems can be operational with numerous other general purpose or special purpose computing system environments or configurations. Examples of well-known computing systems, environments, and/or configurations that can be suitable for use with the systems and methods comprise, but are not limited to, personal computers, server computers, laptop devices, and multiprocessor systems. Additional examples comprise set top boxes, programmable consumer electronics, network PCs, minicomputers, mainframe computers, distributed computing environments that comprise any of the above systems or devices, and the like.

The processing of the disclosed methods and systems can be performed by software components. The disclosed systems and methods can be described in the general context of computer-executable instructions, such as program modules, being executed by one or more computers or other devices. Generally, program modules comprise computer code, routines, programs, objects, components, data structures, etc., that perform particular tasks or implement particular abstract data types. The disclosed methods can also be practiced in grid-based and distributed computing environments where tasks are performed by remote processing devices that are linked through a communications network. In a distributed computing environment, program modules can be located in both local and remote computer storage media including memory storage devices.

Further, one skilled in the art will appreciate that the systems and methods disclosed herein can be implemented via an electronics control subsystem (ECS) 300 illustrated in FIG. 13 (the ECS 300 can be thought of as a computer board 300 but contained within the contaminant sensor 20). The components of the ECS 300 can comprise, but are not limited to, one or more processors or processing units 303, a system memory 312, and a system bus 313 that couples various system components including the processor 303 to the system memory 312. In the case of multiple processing units 303, the system can utilize parallel computing.

The system bus 313 represents one or more of several possible types of bus structures, including a memory bus or memory controller, a peripheral bus, an accelerated graphics port, and a processor or local bus using any of a variety of bus architectures. By way of example, such architectures can comprise an Industry Standard Architecture (ISA) bus, a Micro Channel Architecture (MCA) bus, an Enhanced ISA (EISA) bus, a Video Electronics Standards Association (VESA) local bus, an Accelerated Graphics Port (AGP) bus, and a Peripheral Component Interconnects (PCI), a PCI-Express bus, a Personal Computer Memory Card Industry Association (PCMCIA), Universal Serial Bus (USB) and the like. The bus 313, and all buses specified in this description can also be implemented over a wired or wireless network connection and each of the subsystems, including the processor 303, a mass storage device 304, an operating system 305, a detection application 306, detection data 307, a network adapter 308, system memory 312, an Input/Output Interface 310, a display adapter 309, a display device 311, and a human machine interface 302, can be contained within one or more remote computing devices 350 at physically separate locations, connected through buses of this form, in effect implementing a fully distributed system.

The ECS 300 typically comprises a variety of computer readable media. Exemplary readable media can be any available media that is accessible by the ECS 300 and comprises, for example and not meant to be limiting, both volatile and non-volatile media, removable and non-removable media. The system memory 312 comprises computer readable media in the form of volatile memory, such as random access memory (RAM), and/or non-volatile memory, such as read only memory (ROM). The system memory 312 typically contains data such as detection data 307 and/or program modules such as operating system 305 and detection application 306 that are immediately accessible to and/or are presently operated on by the processing unit 303.

In another aspect, the ECS 300 can also comprise other removable/non-removable, volatile/non-volatile computer storage media. By way of example, FIG. 13 illustrates a mass storage device 304, which can provide non-volatile storage of computer code, computer readable instructions, data structures, program modules, and other data for the ECS 300. For example and not meant to be limiting, a mass storage device 304 can be a hard disk, a removable magnetic disk, a removable optical disk, magnetic cassettes or other magnetic storage devices, flash memory cards, CD-ROM, digital versatile disks (DVD) or other optical storage, random access memories (RAM), read only memories (ROM), electrically erasable programmable read-only memory (EEPROM), and the like.

Optionally, any number of program modules can be stored on the mass storage device 304, including by way of example, an operating system 305 and detection application 306. Each of the operating system 305 and detection application 306 (or some combination thereof) can comprise elements of the programming and the detection application 306. Detection data 307 can also be stored on the mass storage device 304. Detection data 307 can be stored in any of one or more databases known in the art. Examples of such databases include DB2®, Microsoft® Access, Microsoft® SQL Server, Oracle®, mySQL, PostgreSQL, and the like. The databases can be centralized or distributed across multiple systems.

In another aspect, the user can enter commands and information into the ECS 300 via an input device (not shown). Examples of such input devices comprise, but are not limited to, a keyboard, a touch screen display 40 (as discussed above), pointing device (e.g., a "mouse"), a microphone, a joystick, a scanner, tactile input devices such as gloves, and other body coverings, and the like. These and other input devices can be connected to the processing unit 303 via a human machine interface 302 that is coupled to the system bus 313, but can be connected by other interface and bus structures, such as a parallel port, game port, an IEEE 1394 Port (also known as a Firewire port), a serial port, or a universal serial bus (USB).

In yet another aspect, a display device 311 can also be connected to the system bus 313 via an interface, such as a display adapter 309. In an aspect, the display device 311 can be combined with a input device (e.g., touch screen display). It is contemplated that the ECS 300 can have more than one display adapter 309 and the ECS 300 can have more than one display device 311. For example, a display device can be a monitor, an LCD (Liquid Crystal Display), or a projector. In addition to the display device 311, other output peripheral devices can comprise components such as speakers (not shown) and a printer (not shown) which can be connected to the EECS 300 via Input/Output Interface 310. Any step and/or result of the methods can be output in any form to an output device. Such output can be any form of visual representation, including, but not limited to, textual, graphical, animation, audio, tactile, and the like.

The ECS 300 can operate in a networked environment using logical connections to one or more remote computing devices 350. By way of example, a remote computing device 350 can be a personal computer, portable computer, a server, a router, a network computer, a peer device or other common network node, and so on. Logical connections between the ECS 300 and a remote computing device 350 can be made via a network 315. The network 315 can include, but is not limited to, a local area network (LAN) and a general wide area network (WAN). Such network connections can be through a network adapter 308. A network adapter 308 can be implemented in both wired and wireless environments. Such networking environments are conventional and commonplace in offices, enterprise-wide computer networks, intranets, and the Internet 315.

For purposes of illustration, application programs and other executable program components such as the operating system 305 are illustrated herein as discrete blocks, although it is recognized that such programs and components reside at various times in different storage components of the ECS 300, and are executed by the data processor(s) of the ECS 300. An implementation of detection application 306 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" comprise volatile and non-volatile, removable and non-removable media implemented in any methods or technology for storage of information such as computer readable instructions, data structures, program modules, or other data. Exemplary computer storage media comprises, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

The methods and systems can employ Artificial Intelligence techniques such as machine learning and iterative learning. Examples of such techniques include, but are not limited to, expert systems, case based reasoning, Bayesian networks, behavior based AI, neural networks, fuzzy systems, evolutionary computation (e.g. genetic algorithms), swarm intelligence (e.g. ant algorithms), and hybrid intelligent systems (e.g. expert inference rules generated through a neural network or production rules from statistical learning).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

The most significant benefit of the carbon dioxide monitoring system 10 is a major reduction in the expense of monitoring for carbon dioxide contaminants. The installation of the carbon dioxide monitoring system 10 will eliminate the need for highly expensive analyzers based on general purpose laboratory equipment using gas chromatography and/or mass spectroscopy. Equipment purchase costs are currently estimated to be between $120,000 and $300,000.

A second benefit is the elimination of the cost and hazard associated with carrier gases, like highly explosive hydrogen, which are needed to operate the gas chromatography-based analyzers.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention. To the extent necessary to understand or complete the disclosure of the present invention, all publications, patents, and patent applications mentioned herein are expressly incorporated by reference therein to the same extent as though each were individually so incorporated.

Having thus described exemplary embodiments of the present invention, those skilled in the art will appreciate that the within disclosures are exemplary only and that various other alternatives, adaptations, and modifications may be made within the scope of the present invention. Accordingly, the present invention is not limited to the specific embodiments as illustrated herein, but is only limited by the following claims.

What is claimed is:

1. A carbon dioxide contaminant monitoring system, comprising:
   a contaminant sensor module comprising an interferometer configured to create an interference pattern based on the presence of contaminants;
   a delivery system for supplying carbon dioxide to the interferometer, the delivery system comprising
   a gas intake port,
   a filtered path in communication with the gas intake port which comprises a contaminant filter configured to remove a contaminant from carbon dioxide passing there through,
   an unfiltered path in communication with the gas intake port which bypasses the containment filter, and
   a selector valve in communication with the filtered path and the unfiltered path which selects either the filtered path or the unfiltered path to be in fluid communication with the interferometer; and
   gas controller module to control the flow of carbon dioxide gas from the delivery system.

2. The carbon dioxide contaminant monitoring system of claim 1, wherein the interferometer further comprises a waveguide, and wherein the delivery system provides the representative flow of the carbon dioxide gas to the waveguide to detect a contaminant.

3. The carbon dioxide contaminant monitoring system of claim 2, wherein the waveguide further comprises at least one sense channel and at least one reference channel.

4. The carbon dioxide contaminant monitoring system of claim 3, wherein the at least one sense channel has a cladding layer with a chemically sensitive polymer configured to change index of refraction based on the presence of a contaminant.

5. The carbon dioxide contaminant monitoring system of claim 4, wherein the at least one reference channel is covered so as not to induce a phase shift in the presence of the contaminants to which the chemically sensitive polymer reacts.

6. The carbon dioxide contaminant monitoring system of claim 5, wherein the interferometer further comprises a camera configured to capture the interference pattern.

7. The carbon dioxide contaminant monitoring system of claim 6, further comprising a system controller, wherein the system controller is configured to determine the presence of a contaminant by determining the phase shift of the captured interference pattern.

8. The carbon dioxide contaminant monitoring system of claim 7, wherein the system controller is configured to determine the phase shift of the captured interference pattern by determining an appropriate measurement zone of the captured interference pattern, determining an interference pattern period within the appropriate measurement zone, determining the phase shift that has occurred from the interference pattern period, and correlating data from the phase shift with calibration data to determine the presence of at least one contaminant.

9. The carbon dioxide contaminant monitoring system of claim 1, wherein the contaminant sensor module is configured to self-calibrate.

10. A carbon dioxide gas contaminant sensor apparatus, comprising:
    an interferometer having two optical paths, wherein the first optical path is configured to change index of refraction based on the presence of a containment/substance and producing an interference pattern;
    a light source directed into the interferometer;
    a gas source supplying a representative flow of gas to the interferometer, the gas source comprising
    a gas intake port,
    a filtered path in communication with the gas intake port which comprises a contaminant filter configured to remove a contaminant from carbon dioxide passing there through,
    an unfiltered path in communication with the gas intake port which bypasses the containment filter, and
    a selector valve in communication with the filtered path and the unfiltered path which selects either the filtered path or the unfiltered path to be in fluid communication with the interferometer;
    a camera; and
    a system controller connected to the camera configured to detect changes in the interference pattern.

11. The carbon dioxide gas contaminant sensor apparatus of claim 10, wherein the first optical path comprises a waveguide channel having a cladding layer with a chemically sensitive polymer.

12. The carbon dioxide gas contaminant sensor apparatus of claim 10, further comprising a flow cell having a gas inlet port and a gas exhaust port, wherein the flow cell directs the gas over the first and second optical paths.

13. The carbon dioxide gas contaminant sensor apparatus of claim 12, further comprising a pump connected to the gas inlet port.

14. The carbon dioxide gas contaminant sensor apparatus of claim 10, wherein the light source is a laser.

15. The carbon dioxide gas contaminant sensor apparatus of claim 10, wherein the camera is a charge-coupled device.

16. The carbon dioxide gas contaminant sensor apparatus of claim 10, further comprising a particulate filter connected to the gas inlet port.

17. A method of sensing contaminants in carbon dioxide gas, comprising:
pumping carbon dioxide gas to be sensed into an interferometer having a first channel configured to change index of refraction in the presence of contaminants and a second channel;
directing light from a light source into the first and second channels of the interferometer;
combining the output of the first and second channels to create an interference pattern;
capturing the interference pattern with a camera;
measuring the phase shift between the first and second channels by analyzing the captured interference pattern; and
calibrating the interferometer by providing either a filtered path and an unfiltered path in fluid communication with the interferometer via a delivery system comprising
a gas intake port,
wherein the filtered path is in communication with the gas intake port which comprises a contaminant filter configured to remove a contaminant from carbon dioxide passing there through,
wherein the unfiltered path is in communication with the gas intake port which bypasses the containment filter, and
a selector valve in communication with the filtered path and the unfiltered path which selects either the filtered path or the unfiltered path to be in fluid communication with the interferometer.

18. The method of sensing contaminants in carbon dioxide gas of claim 17, further comprising comparing the captured interference pattern produced to a reference interference pattern.

19. The method of sensing contaminants in carbon dioxide gas of claim 17, wherein the interferometer further comprises a waveguide having the first and second channel wherein the first channel has a chemically sensitive polymer cladding layer.

* * * * *